United States Patent
Chen et al.

(10) Patent No.: US 6,284,275 B1
(45) Date of Patent: *Sep. 4, 2001

(54) CONTROLLED RELEASE TABLET HAVING A UNITARY CORE

(75) Inventors: Chih-Ming Chen; Xiu Xiu Cheng, both of Davie; Joseph Chou; Steve Jan, both of Coral Springs, all of FL (US)

(73) Assignee: Andrx Pharmaceuticals, Inc., Davie, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/590,807

(22) Filed: Jun. 9, 2000

Related U.S. Application Data

(63) Continuation of application No. 09/143,876, filed on Aug. 31, 1998, now Pat. No. 6,099,862.

(51) Int. Cl.$^7$ .............. A61K 9/20; A61K 9/24; A61K 9/36
(52) U.S. Cl. .......... 424/473; 424/468; 424/474; 424/475; 424/479; 424/480
(58) Field of Search ............... 424/468, 473, 424/474, 475, 479, 480; 514/635, 588, 591, 592, 593

(56) References Cited

U.S. PATENT DOCUMENTS

| | | |
|---|---|---|
| 3,845,770 | 11/1974 | Theeuwes et al. . |
| 3,916,899 | 11/1975 | Theeuwes et al. . |
| 3,952,741 | 4/1976 | Baker . |
| 3,957,853 | 5/1976 | Bohoun . |
| 4,034,758 | 7/1977 | Theeuwes . |
| 4,077,407 | 3/1978 | Theeuwes et al. . |
| 4,080,472 | 3/1978 | Bohoun . |
| 4,522,625 | 6/1985 | Edgren . |
| 4,587,117 | 5/1986 | Edgren et al. . |
| 4,609,374 | 9/1986 | Ayer . |
| 4,612,008 | 9/1986 | Wong et al. . |
| 4,615,698 | 10/1986 | Guittard et al. . |
| 4,624,847 | 11/1986 | Ayer et al. . |
| 4,627,850 | 12/1986 | Deters et al. . |
| 4,692,336 | 9/1987 | Eckenhoff et al. . |
| 4,696,815 | 9/1987 | Schepky et al. . |
| 4,704,118 | 11/1987 | Eckenhoff . |

(List continued on next page.)

FOREIGN PATENT DOCUMENTS

| | | |
|---|---|---|
| 0283369 | 8/1993 | (EP) . |
| 2320735 | 8/1975 | (FR) . |
| 1522179 | 11/1976 | (GB) . |
| 9608243 | 3/1996 | (WO) . |
| 9609823 | 4/1996 | (WO) . |
| 9717975 | 5/1997 | (WO) . |
| 9810786 | 3/1998 | (WO) . |
| 9827982 | 7/1998 | (WO) . |
| WO200028990 * | 5/2000 | (WO) . |
| WO2000289989* | 5/2000 | (WO) . |

OTHER PUBLICATIONS

Clin. Ther. May 1996; 18 (3):pp. 360–371, Campell et al. Briscoe TA, et al.; Dept of Medicine Morehouse of Medicince, Atlanta, GA.
Ann. Intern Med. Feb. 1, 1998; 128 (3) pp. 165–175.
Physicians's Desk Reference 52th Ed. pp. 795–800; 1217–1219 and 2182–2186.

*Primary Examiner*—Thurman K. Page
*Assistant Examiner*—Brian K. Seidleck
(74) *Attorney, Agent, or Firm*—Hedman & Costigan P.C.

(57) ABSTRACT

A controlled release pharmaceutical tablet containing antihyperglycemic drug and a hypoglycemic drug that does not contain an expanding or gelling polymer layer and comprising a core containing the antihyperglycemic drug and the hypoglycemic drug, a semipermeable coating membrane surrounding the core and at least one passageway in the membrane to allow the drugs to be released from the core.

39 Claims, 2 Drawing Sheets

U.S. PATENT DOCUMENTS

| | | |
|---|---|---|
| 4,708,868 | 11/1987 | Brickl et al. . |
| 4,777,049 | 10/1988 | Magruder et al. . |
| 4,803,076 | 2/1989 | Ranade . |
| 4,851,229 | 7/1989 | Magruder et al. . |
| 4,863,724 | 9/1989 | Schepky et al. . |
| 4,865,598 | 9/1989 | Eckenhoff . |
| 4,871,549 | 10/1989 | Ueda et al. . |
| 4,892,739 | 1/1990 | Shah et al. . |
| 4,963,141 | 10/1990 | Eckenhoff . |
| 5,024,843 | 6/1991 | Kuczynski et al. . |
| 5,030,452 | 7/1991 | Curatolo . |
| 5,071,607 | 12/1991 | Ayer et al. . |
| 5,082,668 | 1/1992 | Wong et al. . |
| 5,091,190 | 2/1992 | Kuczyski et al. . |
| 5,108,756 | 4/1992 | Curatolo . |
| 5,110,597 | 5/1992 | Wong et al. . |
| 5,120,548 | 6/1992 | McClelland et al. . |
| 5,141,752 | 8/1992 | Ayer et al. . |
| 5,178,867 | 1/1993 | Guittard et al. . |
| 5,185,158 | 2/1993 | Ayer et al. . |
| 5,260,275 | 11/1993 | Cooper et al. . |
| 5,308,348 | 5/1994 | Balaban et al. . |
| 5,356,913 | 10/1994 | Colca . |
| 5,413,572 | 5/1995 | Wong et al. . |
| 5,512,293 | 4/1996 | Landrau et al. . |
| 5,543,156 | 8/1996 | Roorda et al. . |
| 5,545,413 | 8/1996 | Kuczynski et al. . |
| 5,591,454 | 1/1997 | Kuyczynski et al. . |
| 5,614,578 | 3/1997 | Dong et al. . |
| 5,629,319 | 5/1997 | Luo et al. . |
| 5,631,224 | 5/1997 | Efendic et al. . |
| 5,650,170 | 7/1997 | Wright et al. . |
| 5,667,804 | 9/1997 | Wong et al. . |
| 5,668,117 | 9/1997 | Shapiro . |
| 5,674,900 | 10/1997 | Ubillas et al. . |
| 5,688,518 | 11/1997 | Ayer et al. . |
| 5,691,386 | 11/1997 | Inman et al. . |
| 5,922,769 | * 7/1999 | Barelli et al. . |
| 6,011,049 | * 1/2000 | Whitcomb et al. . |
| 6,031,004 | * 2/2000 | Timmins et al. . |

\* cited by examiner

US 6,284,275 B1

CONTROLLED RELEASE TABLET HAVING A UNITARY CORE

This is a continuation application of Ser. No. 09/143,876 filed Aug. 31, 1998 now U.S. Pat. No. 6,099,862.

BACKGROUND OF THE INVENTION:

The present invention relates to controlled release unit dose formulations containing an antihyperglycemic drug and a hypoglycemic drug. As used in this specification the term "antihyperglycemic" refers to a drug that is useful in controlling or managing noninsulin-dependent diabetes mellitus (NIDDM) by decreasing hepatic glucose production, decreasing intestinal absorption of glucose and/or improving insulin sensitivity. Biguanides are the preferred antihyperglycemic drugs. As used in this specification the term "hypoglycemic" refers to a drug that is useful in controlling or managing noninsulin-dependent diabetes mellitus (NIDDM) by stimulating the release of insulin from the pancreas. Sulfonylureas are the preferred hypoglycemic drugs.

In a preferred embodiment, the present invention relates to an oral dosage form comprising a unique combination of a biguanide and a sulfonylurea. The biguanide is preferably metformin or buformin or a pharmaceutically acceptable salt thereof such as metformin hydrochloride or the mefformin salts described in U.S. Pat. Nos. 3,957,853 and 4,080,472 which are incorporated herein by reference. The sulfonylurea compound is preferably glipizide as described in U.S. Pat. No. 5,545,413 or glyburide. Other possible sulfonylurea compounds such as glibornuride, glisoxepide, gliclazide acetohexamide, chlorpropamide, tolazamide, tolbutamide and tolbutamide which are described in U.S. Pat. Nos. 5,674,900 and 4,708,868, which are incorporated herein by reference, may also be employed.

The dosage form of the present invention can provide therapeutic levels of the drugs from twelve to twenty-four hour periods. In a preferred embodiment, the dosage form will be administered once a day and provide therapeutic levels of the drug throughout the day.

In the prior art, many techniques have been used to provide controlled and extended-release pharmaceutical dosage forms in order to maintain therapeutic serum levels of medicaments and to minimize the effects of missed doses of drugs caused by a lack of patient compliance.

In the prior art are extended release tablets which employ either a biguanide drug alone or a sulfonylurea drug alone. For example WO 96/08243 discloses a controlled release dosage form containing only metformin HCl, a biguanide, as the active ingredient and employs a hydrogel to push the active ingredient from the dosage form. Similarly, U.S. Pat. Nos. 5,545,413, 5,591,454 and 5,091,190 disclose controlled release dosage forms containing only the drug glipizide and employ a hydrogel to push the active ingredient from the dosage form.

The 50th edition of the Physicians' Desk Reference®, copyright 1996, suggests administering to a patient a metformin HCl dosage form commercially available from Bristol-Myers Squibb Co. under the tradename GLUCOPHAGE® and a dosage form of a sulfonylurea compound such as glyburide. More specifically, page 753 of the 50th edition of the Physicians' Desk Reference states that if adequate glycemic control is not attained with GLUCOPHAGE® monotherapy, the combination of GLUCOPHAGE® and a sulfonylurea such as glyburide may have a synergistic effect, since both active ingredients act to improve glucose tolerance by different mechanism. According to the 50th edition of the Physicians' Desk Reference, the GLUCOPHAGE® dosage form is believed to function by decreasing hepatic glucose production, decreasing intestinal absorption of glucose and improving insulin sensitivity, while the sulfonylurea compound is believed to lower the blood glucose levels by stimulating the release of insulin from the pancreas.

Although the 50th edition of the Physicians' Desk Reference suggests the combined administration of mefformin HCl and a sulfonylurea compound, it fails to suggest a single unitary controlled release dosage form comprising both an antihyperglycemic drug and a hypoglycemic drug that can provide continuous and non-pulsating therapeutic levels of an antihyperglycemic drug and a hypoglycemic drug to an animal in need of such treatment over a twelve hour or twenty-four hour period.

It is an object of the present invention to provide a controlled or sustained release formulation that contains both an antihyperglycemic drug and a hypoglycemic drug.

It is a further object of the present invention to provide a controlled or sustained release formulation that contains both an antihyperglycemic drug and a hypoglycemic drug that does not employ an expanding or gel forming material to push the drugs out.

It is a further object of the present invention to provide a controlled or sustained release formulation that contains both an antihyperglycemic drug and a hypoglycemic drug that can provide continuous and non-pulsating therapeutic levels of an antihyperglycemic drug to an animal in need of such treatment over a twelve hour or twenty-four hour period.

It is also an object of this invention to provide a controlled or sustained release pharmaceutical tablet having a homogeneous core wherein the core component may be made using ordinary tablet compression techniques.

SUMMARY OF THE INVENTION

The foregoing objectives are meet by a controlled release dosage form which comprises:
 (a) a core which comprises:
  (i) an antihyperglycemic drug;
  (ii) a hypoglycemic drug;
  (iii) a binding agent; and
  (iv) optionally, an absorption enhancer;
 (b) optionally a seal coating layer around the core;
 (c) a semipermeable coating membrane surrounding the core; and
 (d) at least one passageway in the semipermeable membrane to allow release of the antihyperglycemic drug and the hypoglycemic drug.

In the preferred embodiment the antihyperglycemic drug is a biguanide such as metformin or a pharmaceutically acceptable salt and the hypoglycemic drug is a sulfonylurea, such as glipizide or a pharmaceutically acceptable salt thereof.

DETAILED DESCRIPTION OF THE INVENTION

Figure 1:
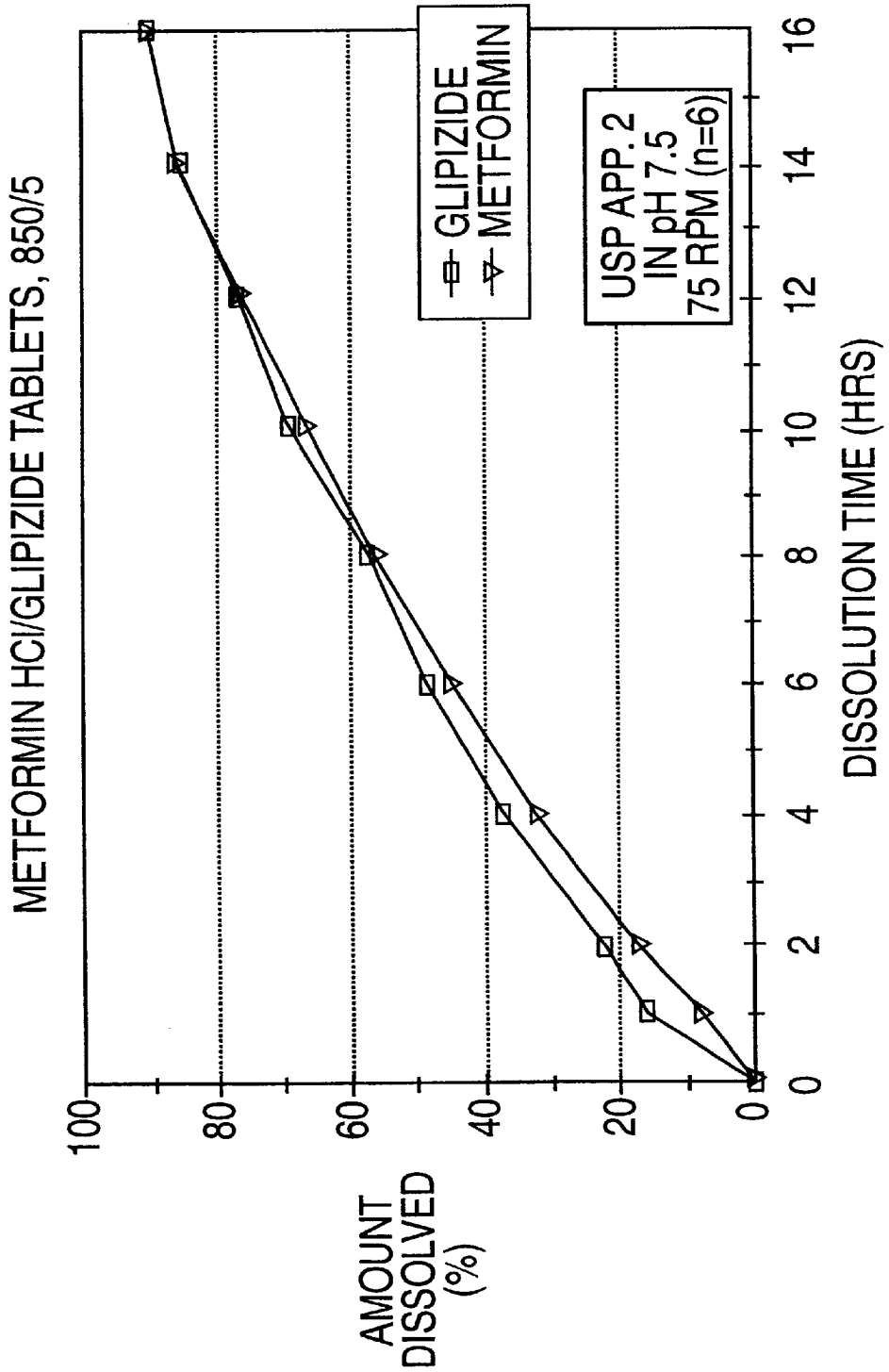
FIG. 1 is a graph which depicts the dissolution profile in simulated intestinal fluid (SIF), pH 7.5 phosphate buffer of the formulation described in Example 1 as tested according to the procedure described in United States Pharmacopeia XXIII, Apparatus 2@75 rpm.

The term antihyperglycemic drug as used in this specification refers to drugs that are useful in controlling or managing noninsulin-dependent diabetes mellitus (NIDDM) by decreasing hepatic glucose production, decreasing intestinal absorption of glucose and/or improving insulin sensitivity. Preferably the antihyperglycemic drug is a biguanide such as metformin or buformin or a pharmaceutically acceptable salt thereof such as metformin hydrochloride.

The term hypoglycemic drug as used in this specification refers to drugs that are useful in controlling or managing noninsulin-dependent diabetes mellitus (NIDDM) by stimulating the release of insulin from the pancreas. Preferably the hypoglycemic drug is a sulfonylurea compound such as glyburide, glipizide, glibornuride, glisoxepide, gliclazide, acetohexamide, chlorpropamide, tolazamide, tolbutamide, tolbutamide or mixtures thereof.

The binding agent may be any conventionally known pharmaceutically acceptable binder, but it is preferred that the binding agent be a water-soluble polymer such as polyvinyl pyrrolidone having a weight average molecular weight of 25,000 to 200,000. Other pharmaceutically acceptable water-soluble polymers include hydroxypropyl cellulose, hydroxyethyl cellulose, hydroxypropyl methylcellulose and the like. Mixtures of the water-soluble binders may also be used. The water-soluble binders comprise approximately about 0 to about 40% of the total weight of the core and preferably about 3–15% of the total weight of the core.

The absorption enhancer employed in the core can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants, especially alkyl sulfates, such as sodium lauryl sulfate, sodium dodecyl sulfate and polysorbate 80, chelating agents such as citric acid and phytic acid. The core comprises approximately 1 to about 20% absorption enhancer based on the total weight of the core and most preferably about 2 to about 10% of the total weight of the core.

The core of the present invention which comprises the antihyperglycemic drug, the hypoglycemic drug, the binder which preferably is a pharmaceutically acceptable water-soluble polymer and the absorption enhancer is preferably formed by mixing and tableting techniques commonly known in the art. The core may also be formed by granulating the core ingredients and compressing the granules with or without the addition of a lubricant into a tablet. The tableting can be performed on a rotary press.

Other commonly known excipients may also be included into the core such as lubricants, pigments or dyes.

The homogeneous core is subsequently coated with a semipermeable membrane, preferably a modified polymeric membrane to form the controlled release tablet of the invention. The semipermeable membrane is permeable to the passage of an external fluid such as water and biological fluids and is impermeable to the passage of the antihyperglycemic drug and/or the hypoglycemic drug in the core. Materials that are useful in forming the semipermeable membrane are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, cellulose acetate butyrate and ethylcellulose. Other suitable polymers are described in U.S. Pat. Nos. 3,845,770, 3,916,899, 4,008,719, 4,036,228 and 4,11210 which are incorporated herein by reference. The most preferred semipermeable membrane material is cellulose acetate comprising an acetyl content of 39.3 to 40.3%, commercially available under the tradename CA 398-10 or CA 398-3 from Eastman Fine Chemicals.

In an alternative embodiment, the semipermeable membrane can be formed from the above-described polymers and a flux enhancing agent. The flux enhancing agent increase the volume of fluid imbibed into the core to enable the dosage form to dispense substantially all of the antihyperglycemic drug and hypoglycemic drug through both the passageway and the porous membrane. The flux enhancing agent is a water-soluble component such as sodium chloride, potassium chloride, sugar, sucrose, sorbitol, mannitol, polyethylene glycol (weight av. molecular weight 380–3700), propylene glycol, hydroxypropyl cellulose, hydroxypropyl methylcellulose and mixtures thereof. The preferred flux enhancer is PEG 400.

The flux enhancing agent comprises approximately 0 to 40% of the total weight of the coating, most preferably 2–20% of the total weight of the coating. The flux enhancing agent dissolves or leaches from the semipermeable membrane to form paths in the semipermeable membrane for the fluid to enter the core and dispense the active ingredients from the core.

The semipermeable membrane may also be formed with commonly known excipients such a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizer is triacetin but materials such as acetylated monoglyceride, rape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0% to 25%, and preferably 2 to 15% of the plasticizer can be used based upon the total weight of the coating.

As used herein the term passage way includes an aperture, orifice, bore, hole, weaken area or an erodible element such as a gelatin plug that erodes to form an osmotic passage way for the release of the antihyperglycemic drug and hypoglycemic drug from the dosage form. A detailed description of the passageway can be found in U.S. Pat. Nos. 3,845,770, 3,916,899, 4,034,758, 4,077,407, 4,783,337 and 5,071,607.

Generally, the membrane coating around the core will comprise from about 1–10% (theoretically) and preferably about 2–6% (theoretically) based on the total weight of the core and coating.

In a preferred embodiment the dosage form will have the following composition:

|  | Preferred | Most Preferred |
|---|---|---|
| CORE: | | |
| antihyperglycemic cpd | 50–96% | 75–93% |
| hypoglycemic cpd | 0.05–3% | 0.25–2% |
| binder | 0–40% | 3–15% |
| absorption enhancer | 1–20% | 2–10% |
| COATING: | | |
| semipermeable polymer | 50–99% | 75–95% |
| plasticizer | 0–25% | 2–15% |
| flux enhancer | 0–40% | 2–20% |

The dosage forms prepared according to the present invention should exhibit the following dissolution profile when tested in a USP type 2 (paddle) apparatus at 75 rpms in 900 ml of simulated intestinal fluid (pH 7.5 phosphate buffer) and at 37° C.:

| ANTIHYPERGLYCEMIC RELEASE | | |
|---|---|---|
| Time (hours) | Preferred | Most Preferred |
| 2 | 0–30% | 0–25% |
| 4 | 10–50% | 20–45% |
| 8 | 30–90% | 45–90% |
| 12 | NLT 50% | NLT 60% |
| 16 | NLT 60% | NLT 70% |

NLT = NOT LESS THAN

| 10/23 HYPOGLYCEMIC RELEASE | | |
|---|---|---|
| Time (hours) | Preferred | Most Preferred |
| 2 | 0–30% | 0–25% |
| 4 | 10–50% | 20–45% |
| 8 | 30–90% | 45–90% |
| 12 | NLT 50% | NLT 60% |
| 16 | NLT 60% | NLT 70% |

NLT = NOT LESS THAN

In the preparation of the tablets of the invention, various conventional well known solvents may be used to prepare the granules and apply the external coating to the tablets of the invention. In addition, various diluents, excipients, lubricants, dyes, pigments, dispersants etc. which are disclosed in Remington's Pharmaceutical Sciences, 1995 Edition may be used to optimize the formulations of the invention. In the alternative, dry granulation techniques may be used to prepare the granules for making compressed tablets.

DESCRIPTION OF THE PREFERRED EMBODIMENTS

EXAMPLE 1

A once a day controlled release tablet containing 850 mg of metformin HCl and 5 mg of glipizide and having the following formula is prepared as follows:

| Core | Weight % |
|---|---|
| metformin HCl | 88.10% |
| glipizide | 0.52% |
| povidone[1], USP | 6.33% |
| sodium lauryl sulfate | 4.56% |
| magnesium stearate | 0.50% |

[1]approximate molecular weight 1,000,000; dynamic viscosity (10% w/v solution at 20° C.) = 300–700 m Pa s.

(a) Granulation 1321.46 g of metformin HCl and 67.01 g of sodium lauryl sulfate are delumped by passing the compounds through a 40 mesh screen and then mixed. 94.92 g of povidone, K-90, and 1.34 g of sodium lauryl sulfate are dissolved in 1,803.5 g of purified water and then 7.76 g of glipizide is dispersed in the solution. The mixture of metformin HCl and sodium lauryl sulfate is then added to a top-spray fluidized bed granulator and granulated by spraying with the granulating solution of povidone, sodium lauryl sulfate and glipizide under the following conditions: product temperature: 35–45° C.; atomization pressure: 1–3 bar; spray rate: 10–150 ml/min. Once the granulating solution is depleted and the granules are dried in the fluidized bed coater until the loss on drying is less than 2%. The dried granules are then passed through a Comil equipped with a screen equivalent to 18 mesh.

(b) Tableting 7.50 g of magnesium stearate is passed through a 40 mesh stainless steel screen and blended with the metformin HCl/glipizide granules for approximately five (5) minutes. After blending, the granules are compressed on a rotary press fitted with 15/32"round standard concave punches.

(c) Seal Coating (optional)

The tablet or core is seal coated with an Opadry material or other suitable water-soluble material by first dissolving the Opadry material, preferably Opadry clear in purified water. The Opadry solution is then sprayed onto the tablet or core using a pan coater under the following conditions: exhaust air temperature of 38–42° C.; atomization pressure of 28–40 psi; and spray rate of 10–150 ml/min. The core tablets are coated with the seal coating until a theoretical coating level of approximately 2% is obtained.

| Sustained Release Coating | Weight % |
|---|---|
| cellulose acetate (398-10)[2] | 85% |
| triacetin | 5% |
| PEG 400[3] | 10% |

[2]acetyl content 39.3–40.3%
[3]weight av. molecular weight 380–420

(d) Sustained Release Coating

The cellulose acetate is dissolved in acetone while stirring with a homogenizer. The polyethylene glycol 400 and triacetin are added to the cellulose acetate solution and stirred until a homogenous solution is obtained. The coating solution is then sprayed onto the seal coated tablets in a fluidized bed coater employing the following conditions: product temperature of 15–25° C; atomization pressure of approximately 1–2 bar; and a spray rate of 10–30 ml/min. This coating process continues until a theoretical coating level of approximately 3% is obtained.

Once the theoretical coating level is obtained, the sustained release coated tablets are dried in the fluidized bed coater for approximately 5 to 10 minutes. Then one hole is either mechanically drilled or laser drilled onto each side of the sustained release tablet.

The resulting tablets are tested in simulated intestinal fluid (pH 7.5) according to the procedure described in United States Pharmacopeia XXIII, Apparatus 2 (paddle) @ 75 rpm and found to have the following release profile:

| TIME (hours) | % Released (pH 7.5) METFORMIN HCl RELEASE |
|---|---|
| 2 | 17 |
| 4 | 32 |
| 8 | 56 |
| 12 | 76 |
| 16 | 89 |
| | GLIPIZIDE RELEASE |
| 2 | 22 |
| 4 | 37 |
| 8 | 57 |
| 12 | 76 |
| 16 | 90 |

The release profile in simulated intestinal fluid (pH 7.5) of the sustained release product prepared in this Example is shown in FIG. 1.

EXAMPLE 2

A controlled release tablet containing 500 mg of metformin HCl and 5 mg of glipizide and having the following formula is prepared as follows:

| Core | Weight % |
|---|---|
| metformin HCl | 87.77% |
| glipizide | 0.88% |
| povidone[4], USP | 6.31% |
| sodium lauryl sulfate | 4.54% |
| magnesium stearate | 0.50% |

[4]approximate molecular weight = 1,000,000 dynamic viscosity (10% w/v solution at 20° C.) = 300–700 m Pa s.

(a) Granulation 5.266 kg of metformin HCl and 0.263 kg of sodium lauryl sulfate are delumped by passing the compounds through a 40 mesh screen and then mixed. 0.379 kg of povidone, K-90, 0.009 kg of sodium lauryl sulfate are dissolved in 7.201 kg of purified water and then 0.053 kg of glipizide is dispersed in the solution. The mixture of mefformin HCl and sodium lauryl sulfate is then added to a top-spray fluidized bed granulator and granulated by spraying with the granulating solution of povidone, sodium lauryl sulfate and glipizide under the following conditions: product temperature: 35–45° C; atomization pressure: 1–3 bar; spray rate: 10–150 ml/min. Once the granulating solution is depleted and the granules are dried in the fluidized bed coater until the loss on drying is less than 2%. The dried granules are then passed through a Comil equipped with a screen equivalent to 18 mesh.

(b) Tableting

The granules are pressed into tablets according to the procedure outlined in Example 1 with the exception that 0.030 kg of magnesium stearate is employed.

(c) Seal Coating (optional)

The tablets are seal coated with an Opadry material or other suitable water-soluble material according to the procedure outlined in Example 1.

| Sustained Release Coating | Weight % |
|---|---|
| cellulose acetate (398-10)[5] | 85% |
| triacetin | 5% |
| PEG 400[6] | 10% |

[5]acetyl content 39.3–40.3%
[6]weight av. molecular weight 380–420

(d) Sustained Release Coating

The sustained release coating solution is prepared and applied to the seal coated tablets according to the procedure outlined in Example 1, with the exception that the sustained release coating is applied to the seal coated tablets until a theoretical coating level of approximately 4.5% is obtained.

The resulting tablet is tested in simulated intestinal fluid (pH 7.5) according to the procedure described in United States Pharmacopeia XXIII, Apparatus 2 (paddle) @ 75 rpm and found to have the following release profile:

| TIME (hours) | % Released (pH 7.5) METFORMIN HCl RELEASE |
|---|---|
| 2 | 23 |
| 4 | 41 |
| 8 | 70 |
| 12 | 92 |
| 16 | 98 |
| | GLIPIZIDE RELEASE |
| 2 | 23 |
| 4 | 35 |
| 8 | 56 |
| 12 | 75 |
| 16 | 90 |

Figure 2:
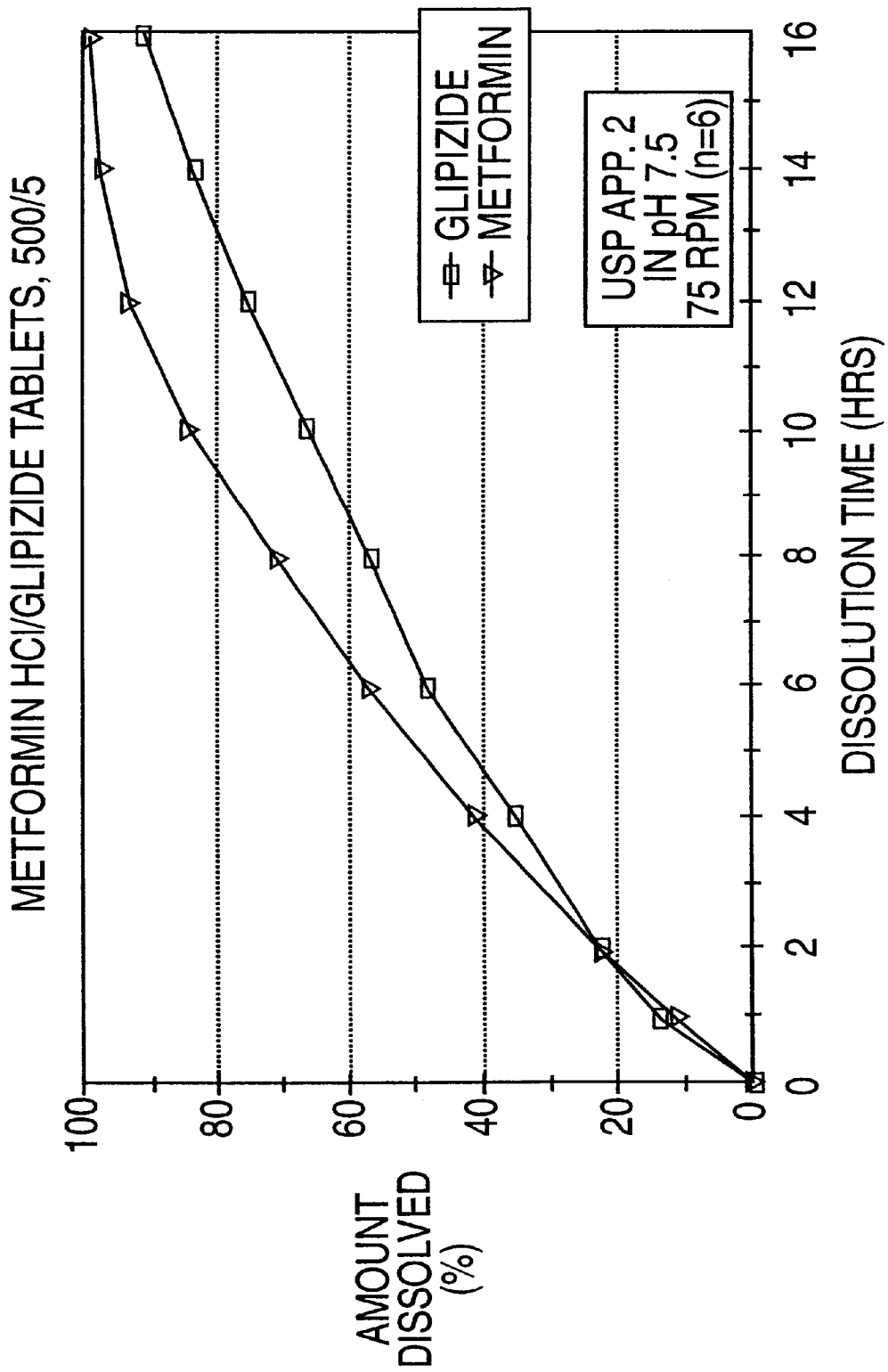
FIG. 2 is a graph which depicts the dissolution profile in simulated intestinal fluid (SIF), pH 7.5 phosphate buffer of the formulation described in Example 2 as tested according to the procedure described in United States Pharmacopeia XXIII, Apparatus 2@75 rpm.

The release profile in SIF of the sustained release product prepared in this Example is shown in FIG. 2.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pharmaceutical tablet consisting essentially of:
   (a) a core consisting essentially of:
      (i) buformin or a pharmaceutically acceptable salt thereof;
      (ii) glipizide;
      (iii) polyvinyl pyrrolidone; and
      (iv) sodium lauryl sulfate;
   (b) optionally, a seal coat around the core;
   (c) a semipermeable membrane coating covering said core comprising;
      (i) cellulose acetate;
      (ii) polyethylene glycol with an average molecular weight between 380 and 420; and
      (iii) a plasticizer; and
   (d) at least one passageway in the semipermeable membrane to allow release of the buformin or a pharmaceutically acceptable salt thereof and glipizide from the core to the environment of use to provide therapeutic levels of buformin or a pharmaceutically acceptable salt thereof and glipizide for from 12 to 24 hours.

2. A controlled release pharmaceutical tablet as defined in claim 1 wherein the absorption enhancer is selected from the group consisting of fatty acids, surfactants, chelating agents, bile salts and mixtures thereof.

3. A controlled release pharmaceutical as defined in claim 1 wherein the absorption enhancer is a fatty acid selected from the group consisting of capric acid, oleic acid and their monoglycerides.

4. A controlled release pharmaceutical tablet as defined in claim 1 wherein the absorption enhancer is a chelating agent selected from the group consisting of citric acid and phytic acid.

5. A controlled release pharmaceutical tablet as defined in claim 1 wherein the absorption enhancer is a bile salt.

6. A controlled release pharmaceutical tablet as defined in claim 1 wherein the semipermeable membrane around the core is cellulose acetate.

7. A controlled release pharmaceutical tablet as defined in claim 1 wherein the semipermeable membrane includes a flux enhancer.

8. A controlled release pharmaceutical tablet as defined in claim 1 wherein the flux enhancer is sodium chloride, potassium chloride, sugar, sucrose, sorbitol, mannitol, polyethylene glycol, propylene glycol, hydroxypropyl cellulose and mixtures thereof.

9. A controlled release pharmaceutical tablet as defined in claim 8 wherein the flux enhancer is polyethylene glycol with an average molecular weight between 380 and 420.

10. A controlled release pharmaceutical tablet as defined in claim 1 wherein the semipermeable membrane comprises a plasticizer.

11. A controlled release pharmaceutical tablet as defined in claim 1 wherein at least two passageways are formed in the semipermeable membrane.

12. A controlled release pharmaceutical tablet as defined in claim 1 that exhibits the following dissolution profile when tested in a USP type 2 paddle apparatus at 75 rpm in 900 ml of simulated intestinal fluid, pH 7.5 phosphate buffer, at 37° C.:

after 2 hours 0–30% of the buformin is released;
after 4 hours 10–50% of the buformin is released;
after 8 hours 30–90% of the buformin is released;
after 12 hours not less than 50% of the buformin is released;
after 16 hours not less than 60% of the buformin is released and
after 2 hours 0–30% of the glipizide is released;
after 4 hours 10–50% of the glipizide is released;
after 8 hours 30–90% of the glipizide is released;
after 12 hours not less than 50% of the glipizide is released;
after 16 hours not less than 60% of the glipizide is released.

13. A controlled release pharmaceutical tablet as defined in claim 11 that exhibits the following dissolution profile when tested in a USP type 2 paddle apparatus at 75 rpms in 900 of simulated intestinal fluid, pH 7.5 phosphate buffer, at 37° C.:

after 2 hours 0–25% of the buformin is released;
after 4 hours 20–45% of the buformin is released;
after 8 hours 45–90% of the buformin is released;
after 12 hours not less than 60% of the buformin is released;
after 16 hours not less than 90% of the buformin is released and
after 2 hours 0–25% of the glipizide is released;
after 4 hours 20–45% of the glipizide is released; after 8 hours 45–90% of the glipizide is released;
after 12 hours not less than 60% of the glipizide is released;
after 16 hours not less than 70% of the glipizide is released.

14. A controlled release pharmaceutical tablet consisting essentially of:
(a) a core consisting essentially of:
(i) metformin or a pharmaceutically acceptable salt thereof;
(ii) glyburide;
(iii) polyvinyl pyrrolidone; and
(iv) sodium lauryl sulfate;
(b) optionally, a seal coat around the core;
(c) a semipermeable membrane coating covering said core comprising;
(i) cellulose acetate;
(ii) polyethylene glycol with an average molecular weight between 380 and 420; and
(iii) a plasticizer; and
(d) at least one passageway in the semipermeable membrane to allow release of the metformin or a pharmaceutically acceptable salt thereof and glyburide from the core to the environment of use to provide therapeutic levels of metformin or a pharmaceutically acceptable salt thereof and glyburide for from 12 to 24 hours.

15. A controlled release pharmaceutical tablet consisting essentially of:
(a) a core consisting essentially of:
(i) buformin or a pharmaceutically acceptable salt thereof;
(ii) glyburide;
(iii) polyvinyl pyrrolidone; and
(iv) sodium lauryl sulfate;
(b) optionally, a seal coat around the core;
(c) a semipermeable membrane coating covering said core comprising;
(i) cellulose acetate;
(ii) polyethylene glycol with an average molecular weight between 380 and 420; and
(iii) a plasticizer; and
(d) at least one passageway in the semipermeable membrane to allow release of the buformin or a pharmaceutically acceptable salt thereof and glyburide from the core to the environment of use to provide therapeutic levels of buformin or a pharmaceutically acceptable salt thereof and glyburide for from 12 to 24 hours.

16. A controlled release pharmaceutical tablet as defined in claim 14 wherein the absorption enhancer is selected from the group consisting of fatty acids, surfactants, chelating agents, bile salts and mixtures thereof.

17. A controlled release pharmaceutical as defined in claim 14 wherein the absorption enhancer is a fatty acid selected from the group consisting of capric acid, oleic acid, and their monoglycerides.

18. A controlled release pharmaceutical tablet as defined in claim 14 wherein the absorption enhancer is a chelating agent selected from the group consisting of citric acid and phytic acid.

19. A controlled release pharmaceutical tablet as defined in claim 14 wherein the absorption enhancer is a bile salt.

20. A controlled release pharmaceutical tablet as defined in claim 14 wherein the semipermeable membrane around the core is cellulose acetate.

21. A controlled release pharmaceutical tablet as defined in claim 14 wherein the semipermeable membrane includes a flux enhancer.

22. A controlled release pharmaceutical tablet as defined in claim 14 wherein the flux enhancer is sodium chloride, potassium chloride, sugar, sucrose, sorbitol, mannitol, polyethylene glycol, propylene glycol, hydroxypropyl cellulose and mixtures thereof.

23. A controlled release pharmaceutical tablet as defined in claim 22 wherein the flux enhancer is polyethylene glycol with an average molecular weight between 380 and 420.

24. A controlled release pharmaceutical tablet as defined in claim 14 wherein the semipermeable membrane comprises a plasticizer.

25. A controlled release pharmaceutical tablet as defined in claim 14 wherein at least two passageways are formed in the semipermeable membrane.

26. A controlled release pharmaceutical tablet as defined in claim 14 that exhibits the following dissolution profile when tested in a USP type 2 paddle apparatus at 75 rpm in 900 ml of simulated intestinal fluid, pH 7.5 phosphate buffer, at 37° C.:
   after 2 hours 0–30% of the metformin is released;
   after 4 hours 10–50% of the metformin is released;
   after 8 hours 30–90% of the metformin is released;
   after 12 hours not less than 50% of the metformin is released;
   after 16 hours not less than 60% of the metformin is released and
   after 2 hours 0–30% of the urea glyburide is released;
   after 4 hours 10–50% of the glyburide is released;
   after 8 hours 30–90% of the glyburide is released;
   after 12 hours not less than 50% of the glyburide is released;
   after 16 hours not less than 60% of the glyburide is released.

27. A controlled release pharmaceutical tablet as defined in claim 14 that exhibits the following dissolution profile when tested in a USP type 2 paddle apparatus at 75 rpms in 900 of simulated intestinal fluid, pH 7.5 phosphate buffer, at 37° C.:
   after 2 hours 0–25% of the metformin is released;
   after 4 hours 20–45% of the metformin is released;
   after 8 hours 45–90% of the metformin is released;
   after 12 hours not less than 60% of the metformin is released;
   after 16 hours not less than 90% of the metformin is released and
   after 2 hours 0–25% of the glyburide is released;
   after 4 hours 20–45% of the glyburide is released;
   after 8 hours 45–90% of the glyburide is released;
   after 12 hours not less than 60% of the glyburide is released;
   after 16 hours not less than 70% of the glyburide is released.

28. A controlled release pharmaceutical tablet as defined in claim 15 wherein the absorption enhancer is selected from the group consisting of fatty acids, surfactants chelating agents, bile salts and mixtures thereof.

29. A controlled release pharmaceutical as defined in claim 15 wherein the absorption enhancer is a fatty acid selected from the group consisting of capric acid, oleic acid, and their monoglycerides.

30. A controlled release pharmaceutical tablet as defined in claim 15 wherein the absorption enhancer is a chelating agent selected from the group consisting of citric acid and phytic acid.

31. A controlled release pharmaceutical tablet as defined in claim 15 wherein the absorption enhancer is a bile salt.

32. A controlled release pharmaceutical tablet as defined in claim 15 wherein the semipermeable membrane around the core is cellulose acetate.

33. A controlled release pharmaceutical tablet as defined in claim 15 wherein the semipermeable membrane includes a flux enhancer.

34. A controlled release pharmaceutical tablet as defined in claim 15 wherein the flux enhancer is sodium chloride, potassium chloride, sugar, sucrose, sorbitol, mannitol, polyethylene glycol, propylene glycol, hydroxypropyl cellulose and mixtures thereof.

35. A controlled release pharmaceutical tablet as defined in claim 33 wherein the flux enhancer is polyethylene glycol with an average molecular weight between 380 and 420.

36. A controlled release pharmaceutical tablet as defined in claim 15 wherein the semipermeable membrane comprises a plasticizer.

37. A controlled release pharmaceutical tablet as defined in claim 15 wherein at least two passageways are formed in the semipermeable membrane.

38. A controlled release pharmaceutical tablet as defined in claim 15 that exhibits the following dissolution profile when tested in a USP type 2 paddle apparatus at 75 rpm in 900 ml of simulated intestinal fluid, pH 7.5 phosphate buffer, at 37° C.:
   after 2 hours 0–30% of the buformin is released;
   after 4 hours 10–50% of the buformin is released;
   after 8 hours 30–90% of the buformin is released;
   after 12 hours not less than 50% of the buformin is released;
   after 16 hours not less than 60% of the buformin is released and
   after 2 hours 0–30% of the urea glyburide is released;
   after 4 hours 10–50% of the glyburide is released;
   after 8 hours 30–90% of the glyburide is released;
   after 12 hours not less than 50% of the glyburide is released;
   after 16 hours not less than 60% of the glyburide is released.

39. A controlled release pharmaceutical tablet as defined in claim 15 that exhibits the following dissolution profile when tested in a USP type 2 paddle apparatus at 75 rpms in 900 of simulated intestinal fluid, pH 7.5 phosphate buffer, at 37° C.:
   after 2 hours 0–25% of the buformin is released;
   after 4 hours 20–45% of the buformin is released;
   after 8 hours 45–90% of the buformin is released;
   after 12 hours not less than 60% of the buformin is released;
   after 16 hours not less than 90% of the buformin is released and
   after 2 hours 0–25% of the glyburide is released;
   after 4 hours 20–45% of the glyburide is released;
   after 8 hours 45–90% of the glyburide is released;
   after 12 hours not less than 60% of the glyburide is released;
   after 16 hours not less than 70% of the glyburide is released.

* * * * *